United States Patent
Reinmuth et al.

(10) Patent No.: US 10,094,725 B2
(45) Date of Patent: Oct. 9, 2018

(54) PRODUCTION METHOD FOR A DETECTION APPARATUS AND DETECTION APPARATUSES

(71) Applicant: Robert Bosch GmbH, Stuttgart (DE)

(72) Inventors: Jochen Reinmuth, Reutlingen (DE); Timo Lindemann, Reutlingen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 165 days.

(21) Appl. No.: 15/408,961

(22) Filed: Jan. 18, 2017

(65) Prior Publication Data

US 2017/0205301 A1 Jul. 20, 2017

(30) Foreign Application Priority Data

Jan. 20, 2016 (DE) .......................... 10 2016 200 699

(51) Int. Cl.
*G01L 9/00* (2006.01)
*H01L 21/00* (2006.01)
(Continued)

(52) U.S. Cl.
CPC .......... *G01L 9/0072* (2013.01); *B81B 7/0074* (2013.01); *B81C 99/004* (2013.01); *G01L 19/147* (2013.01); *G01N 33/00* (2013.01); *H01L 21/563* (2013.01); *H01L 22/10* (2013.01); *H01L 23/315* (2013.01); *H01L 24/49* (2013.01); *H01L 25/165* (2013.01); *H01L 25/50* (2013.01);
(Continued)

(58) Field of Classification Search
CPC ......... G01L 9/00; G01L 9/0072; G01L 19/14; G01L 19/147; H01L 21/00; H01L 21/563; H01L 21/66; H01L 22/10
See application file for complete search history.

(56) References Cited

U.S. PATENT DOCUMENTS

| 4,850,227 A * | 7/1989 | Luettgen ............. G01L 19/0038 73/708 |
| 5,257,547 A * | 11/1993 | Boyer ................. G01L 19/0038 338/4 |
| 6,472,891 B1 | 10/2002 | Tran |

FOREIGN PATENT DOCUMENTS

DE 102007028467 A1 12/2008
DE 202009014795 U1 4/2010
(Continued)

*Primary Examiner* — Nguyen Q. Ha
(74) *Attorney, Agent, or Firm* — Norton Rose Fulbright US LLP; Gerard Messina

(57) ABSTRACT

A production method for a detection apparatus includes: forming at least one sensitive region having at least one exposed sensing area on and/or in a semiconductor substrate, encapsulating at least one part of the semiconductor substrate so that the at least one sensing area is sealed in an air-, liquid- and/or particle-tight fashion from an external environment, and forming at least one opening so that at least one air, liquid and/or particle access from the external environment to the at least one sensing area is created, wherein before forming the at least one opening, at least one first test and/or calibration measurement is performed, for which at least one sensor signal of the at least one sensitive region having the at least one sensing area sealed in an air-, liquid- and/or particle-tight fashion is determined as at least one first test and/or calibration signal. Also described are related detection apparatuses.

12 Claims, 3 Drawing Sheets

(51) Int. Cl.
*H01L 21/66* (2006.01)
*B81B 7/00* (2006.01)
*B81C 99/00* (2010.01)
*G01L 19/14* (2006.01)
*G01N 33/00* (2006.01)
*H01L 21/56* (2006.01)
*H01L 23/00* (2006.01)
*H01L 25/16* (2006.01)
*H01L 25/00* (2006.01)
*H01L 23/31* (2006.01)

(52) U.S. Cl.
CPC ...... *B81C 2203/0136* (2013.01); *H01L 24/48* (2013.01); *H01L 2224/48091* (2013.01); *H01L 2924/00014* (2013.01)

(56) References Cited

FOREIGN PATENT DOCUMENTS

| | | | |
|---|---|---|---|
| DE | 102010064108 A1 | 6/2012 | |
| EP | 0480544 A2 * | 4/1992 | ......... G01L 19/0038 |
| EP | 2009432 A1 | 12/2008 | |
| WO | 2012072347 A1 | 6/2012 | |

\* cited by examiner

US 10,094,725 B2

PRODUCTION METHOD FOR A DETECTION APPARATUS AND DETECTION APPARATUSES

RELATED APPLICATION INFORMATION

The present application claims priority to and the benefit of German patent application no. 10 2016 200 699.1, which was filed in Germany on Jan. 20, 2016, the disclosure of which is incorporated herein by reference.

FIELD OF THE INVENTION

The present invention relates to a production method for a detection apparatus. Furthermore, the present invention relates to detection apparatuses.

BACKGROUND INFORMATION

German patent document DE 10 2010 064 108 A1 discusses a method for packaging a sensor chip for producing a detection apparatus/sensor apparatus. For this purpose, the sensor chip is firstly mounted on a carrier. Afterwards, the sensor chip is at least partly embedded into a moulding compound. Finally, at least one section of a media access to the sensor chip is produced by a subsequent structuring of the moulding compound.

SUMMARY OF THE INVENTION

The present invention provides a production method for a detection apparatus having the features of described herein, a detection apparatus having the features of described herein and a detection apparatus having the features of described herein.

The present invention facilitates production of detection apparatuses, such as sensor apparatuses and amplifier apparatuses, for example, by virtue of the fact that the at least one first test and/or calibration measurement is already carried out before forming the at least one opening for the at least one air, liquid and/or particle access. Consequently, for example, already before forming the at least one opening, on the basis of the at least one first test and/or calibration signal, it is possible to identify whether faults are present on the intermediate product, said faults significantly impairing a later use of the finished produced detection apparatus. If appropriate, the production method can thus be terminated at an early stage, without unnecessary method steps for the further processing of the intermediate product into the finished detection apparatus also being carried out. The air-, liquid- and/or particle-tight sealing of the at least one sensing area of the at least one sensitive region can likewise be used for an advantageous and simply implementable calibration of the detection apparatus, as also explained below. The present invention thus contributes to reducing the production costs for a detection apparatus.

Test costs and calibration costs conventionally make up a considerable proportion of production costs for detection apparatuses. By the present invention, the test costs and calibration costs can be significantly reduced, such that detection apparatuses are producible more cost-effectively.

In one advantageous embodiment of the production method, after forming the at least one opening, at least one second test and/or calibration measurement is carried out, for which purpose the at least one sensor signal of the at least one sensitive region, given the presence of the at least one air, liquid and/or particle access is determined as at least one second test and/or calibration signal of the at least one second test and/or calibration measurement. In particular, the at least one first test and/or calibration signal and the at least one second test and/or calibration signal can be used for an advantageous and cost-effective calibration of the finished produced detection apparatus. By way of example, a detection apparatus configured as a pressure sensor can be calibrated easily and reliably by at least one first test and/or calibration signal measured with the at least one sensing area being present without pressure and at least one second test and/or calibration signal measured with the at least one sensing area being subjected to pressure. Pressure sensors are generally distinguished by a (substantially) linear behaviour, such that the at least one first test and/or calibration signal and the at least one second test and/or calibration signal are sufficient for defining a pressure-dependent detection characteristic, without the need to use a pressure chamber for determining the at least one first test and/or calibration signal or the at least one second test and/or calibration signal.

In one possible embodiment of the production method, the detection apparatus is formed with an evaluation device and a memory, wherein the evaluation device is configured, during the later operation of the detection apparatus, taking account at least of the at least one sensor signal and an evaluation relation stored on the memory, to define and output information regarding the at least one physical variable and/or the at least one substance to be detected, and wherein the evaluation relation is defined at least taking account of the at least one first test and/or calibration signal and is stored on the memory. The calibration of the evaluation device in accordance with this embodiment of the production method can thus be performed easily.

Alternatively, the detection apparatus can be formed with an amplifier device and a memory, wherein the amplifier device is configured, during the later operation of the detection apparatus, taking account of at least the at least one sensor signal and an amplification relation stored on the memory, to output an amplified signal, and wherein the amplification relation is defined at least taking account of the at least one first test and/or calibration signal and is stored on the memory. Consequently, the calibration of the amplifier device such as is carried out in this embodiment of the production method can also be performed easily.

The evaluation relation or the amplification relation may be defined at least taking account of the at least one first test and/or calibration signal and the at least one second test and/or calibration signal. The at least two test and/or calibration signals obtained in a simple manner are sufficient in particular for defining linear relations as the evaluation relation or the amplification relation.

In a further advantageous embodiment of the production method, the at least one sensitive region is formed on and/or in the semiconductor substrate, which is part of a wafer, wherein the semiconductor substrate is structured from the wafer, and wherein at least one item of position information regarding a position of the semiconductor substrate as part of the wafer is concomitantly taken into account by defining the evaluation relation or the amplification relation. Manufacturing fluctuations among the multiplicity of semiconductor substrates obtained from the wafer can be dependent on the respective position thereof as part of the wafer. By a small number of random samples, it is possible to find a reliable matching algorithm by which a manufacturing fluctuation dependent on the position of the respective semiconductor substrate can be compensated for by correspondingly adapted concomitant taking into account when defining the evaluation relation or the amplification relation. The embodiment of the production method described here thus advantageously contributes to the compensation of manufacturing fluctuations in industrial scale production of detection apparatuses.

Advantageously, a pressure sensor, a blood pressure sensor, a sound sensor, a microphone, a temperature sensor, a chemical sensor, a gas sensor, an odour sensor, a liquid sensor and/or a particle sensor can be produced as the detection apparatus. The present invention is thus diversely usable. In particular, all types of sensor enumerated above can be produced even on an industrial scale using the present invention. However, an applicability of the present invention is not limited to the types of sensor enumerated here.

By way of example, a capacitor having a membrane that at least partly spans a cavity formed in the semiconductor substrate can be formed as the at least one sensitive region. This may be done in such a way that a change in a pressure present at the sensing area of the membrane as the at least one physical variable brings about a deformation of the membrane, as a result of which a capacitance of the capacitor varies. A current intensity and/or voltage signal, dependent on the capacitance of the capacitor, as the at least one sensor signal also varies in this case. The embodiment of the production method described here is easily implementable and diversely usable, e.g. for a pressure sensor, a blood pressure sensor, a sound sensor, a microphone and/or a temperature sensor. However, it is pointed out that a configurability of the at least one sensitive region is not restricted to the configuration of the capacitor having the membrane.

The at least one first test and/or calibration signal may be measured with the membrane being present without pressure during the at least one first test and/or calibration measurement. The at least one second test and/or calibration signal may be measured with the membrane being exposed to a pressure not equal to zero, which may be with the membrane being exposed to the atmospheric pressure, during the at least one second test and/or calibration measurement. Primarily a use of the atmospheric pressure for determining the at least one second test and/or calibration signal renders superfluous a use of a pressure chamber for testing/calibrating the finished produced detection apparatus. The testing/calibrating of the finished produced detection apparatus can thus be performed more rapidly and more cost-effectively.

In one advantageous development, a temperature of the membrane can be varied between a plurality of first test and/or calibration measurements and/or between a plurality of second test and/or calibration measurements. Even a temperature-dependent calibration of the detection apparatus can thus be performed simply and rapidly.

The advantages described above can also be realized in the case of the detection apparatuses according to the present invention. It is pointed out that the detection apparatuses according to the present invention can be configured in accordance with the above-described embodiments of the production method.

Further features and advantages of the present invention are explained below with reference to the figures.

DETAILED DESCRIPTION

Figure 1A:
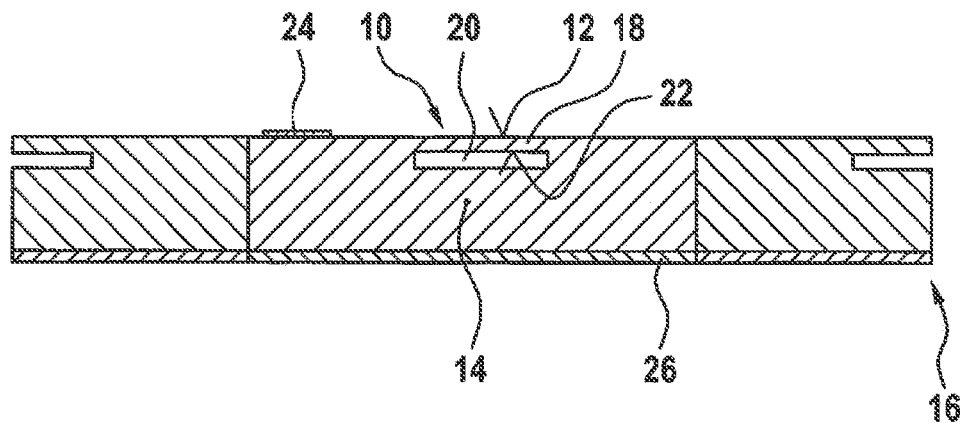
FIGS. 1a, 1b, 1c and 1d show schematic cross sections for elucidating one embodiment of the production method for a detection apparatus.

FIGS. 1a to 1d show schematic cross sections for elucidating one embodiment of the production method for a detection apparatus.

In the embodiment in FIGS. 1a to 1d, at least one pressure sensor is produced as detection apparatus. However, it is pointed out that an implementability of the production method is not limited to producing at least one detection apparatus embodied as a pressure sensor. By way of example, at least one blood pressure sensor, at least one sound sensor, at least one microphone, at least one temperature sensor, at least one chemical sensor (at least one chemical detection sensor and/or at least one chemical concentration measuring instrument), at least one gas sensor, at least one odour sensor, at least one liquid sensor and/or at least one particle sensor can also be produced as the at least one detection apparatus by the (possibly correspondingly adapted) production method. The implementability of the production method is not limited to a specific type of a sensor apparatus and/or an amplifier apparatus as detection apparatus.

Moreover, the production method described here can be performed even on an industrial scale. As can be discerned with reference to FIGS. 1a and 1b, a multiplicity of detection apparatuses can be produced (virtually) simultaneously by the production method described here.

In a method step represented schematically by FIG. 1a, at least one sensitive region 10 having at least one exposed sensing area 12 is formed on and/or in a (later) semiconductor substrate 14. Forming the at least one sensitive region 10 on and/or in a functionalized side of the semiconductor substrate 14 is carried out in such a way that, during later operation of the (finished) detection apparatus, at least one sensor signal of the at least one sensitive region 10 varies in the case of a change in at least one physical variable and/or at least one chemical concentration of at least one substance to be detected at the sensing area 12 of the respective sensitive region 10. The at least one sensor signal can be at least one signal output by the respective sensitive region 10 and/or a signal determined or tapped off at the respective sensitive region 10. By way of example, the at least one sensor signal can be at least one current intensity and/or voltage signal which varies on account of a deformation and/or change of a physical property of at least one subunit of the respective sensitive region 10 which are/is triggered by the change in the at least one physical variable and/or the at least one chemical concentration of the at least one substance to be detected at the sensing area 12. This can also be paraphrased by stating that forming the at least one sensitive region 10 is carried out in such a way that the change in the at least one physical variable and/or the at least one chemical concentration of the at least one substance to be detected at the sensing area 12 brings about the deformation and/or change in the physical property of at least the subunit of the respective sensitive region 10 which are/is determinable by the variation of the at least one sensor signal. In the embodiment in FIGS. 1a to 1d, a multiplicity of sensitive regions 10 are correspondingly formed in a multiplicity of semiconductor substrates 14 (which are singulated later) which are each part of a wafer 16.

By way of example, a capacitor having a membrane 18 that at least partly spans a cavity 20 formed in the semiconductor substrate 14 can be formed as the at least one sensitive region 10. (Depiction of further components of the capacitor has been omitted in FIGS. 1a to 1d for the sake of better clarity.) An area of the assigned membrane 18 that is directed away from the cavity 20 is thus advantageously suitable as a sensing area 12 of the sensitive region 10 formed in this way. A change in a pressure (as the at least one physical variable) present at the sensing area 12 of the membrane 18 can bring about a deformation of the membrane 18, as a result of which a capacitance of the capacitor varies. This triggers a variation of a current intensity and/or voltage signal (as the at least one sensor signal of the respective sensitive region 10) dependent on the capacitance of the capacitor. Since a multiplicity of configuration possibilities for the capacitor are known from the prior art, this will not be discussed in greater detail here.

The configuration of the sensitive region 10 represented in FIG. 1a is well suited to a pressure sensor (absolute pressure sensor) in which a pressure measurement (absolute pressure measurement) can be performed by deformation/flexure of the membrane 18. For this purpose, the pressure to be measured is applied to the sensing area 12 of the membrane 18 while a reference pressure prevailing in the cavity 20 is present on an inner area 22 (directed away from the sensing area 12 and delimiting the cavity 20) of the membrane 18. A vacuum or a very low pressure is expedient as reference pressure in order to limit/avoid an increase in the reference pressure (as a result of expansion of at least one gas present in the cavity 20) in the event of a temperature increase. Since techniques for setting a defined reference pressure in the cavity 20 are already known from the prior art, this is not discussed in greater detail here.

In the embodiment in FIG. 1a, optionally a contact pad 24 is also formed on the functionalized side of the semiconductor substrate 14 (with the membrane 18). Moreover, an optional adhesive layer 26 is deposited on an opposite side (directed away from the functionalized side) of the semiconductor substrate 14. However, depositing the contact pad 24 and/or depositing the adhesive layer 26 are optional method steps.

Figure 1B:
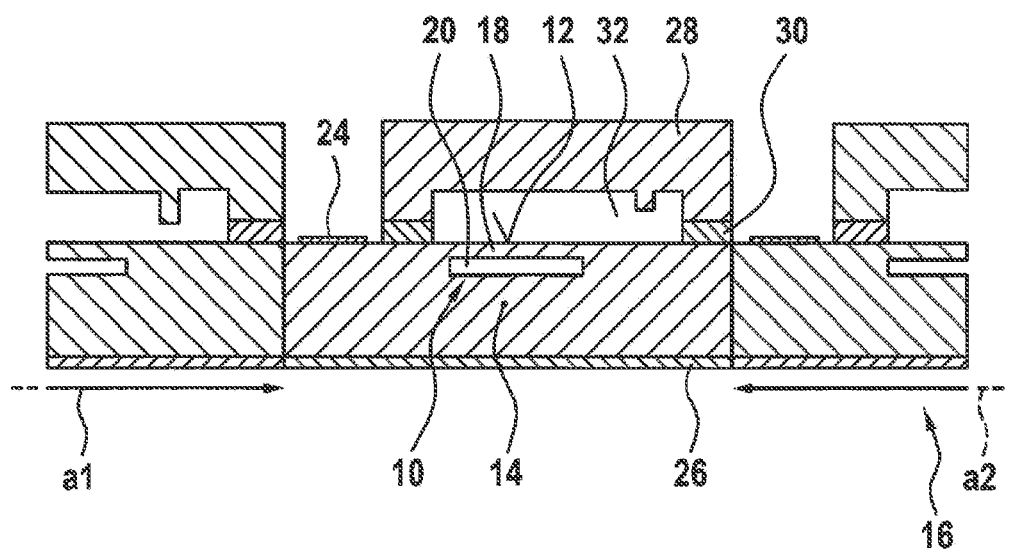

FIG. 1b shows a first method step for encapsulating at least one part of the semiconductor substrate. In the embodiment in FIG. 1b, a (possibly partly hollowed-out) further semiconductor substrate 28 as at least one encapsulation structure 28 is fixed to the semiconductor substrate 14 by at least one bonding and/or adhesive layer 30 such that the encapsulation structure 28 spans the at least one sensitive region 10/the membrane 18. Optionally, a vacuum/a low pressure can be enclosed in an intermediate volume 32 between the at least one sensitive region 10/the membrane 18 and the encapsulation structure 28.

Afterwards, the semiconductor substrate 14 (with the at least one sensitive region 10 on and/or in the semiconductor substrate 14), which is part of the wafer 16, can be structured from the wafer 16. Before the semiconductor substrate 14 is structured therefrom, however, at least one item of position information a1 and a2 regarding a position/location of the semiconductor substrate 14 as part of the wafer 16 can also be defined and/or stored for a later calibration of the semiconductor substrate 14. By way of example, a first distance a1 between the semiconductor substrate 14 and a midpoint (not depicted schematically) of the wafer 16 and/or a second distance a2 between the semiconductor substrate 14 and an edge of the wafer 16 can be defined and/or stored as the at least one item of position information a1 and a2. In this case, the at least one item of position information a1 and a2 can be concomitantly taken into account in a later calibration. (The concomitant taking account of the at least one item of position information a1 and a2 in the calibration of the detection apparatus formed by the respective semiconductor substrate 14 is discussed in even greater detail below.)

Figure 1C:
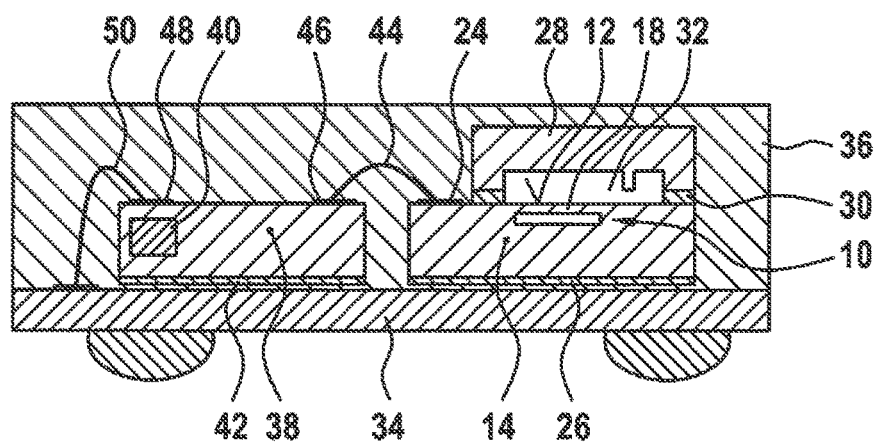

FIG. 1c shows a further method step for encapsulating at least one part of the semiconductor substrate 14 (after the singulation thereof from the wafer 16). For this purpose, the semiconductor substrate 14 is fixed (by the adhesive layer 26) on a printed circuit board 34. Afterwards, at least one encapsulation material 36 (e.g. at least one moulding compound 36) is deposited on the printed circuit board 34 such that the semiconductor substrate 14 (with the encapsulation structure 28) is at least partly (possibly completely) embedded therein. The encapsulation of the semiconductor substrate 14 as illustrated in FIG. 1c has the effect that the at least one sensing area 12 of the at least one sensitive region 10/the membrane 18 is sealed in an air-, liquid- and/or particle-tight fashion from an external environment of the at least partly encapsulated semiconductor substrate. In particular, the at least one sensing area 12 of the at least one sensitive region 10/the membrane 18 is sealed from the external environment by the encapsulation in such a way that even in the case of a (significant) change in the at least one physical variable and/or the at least one chemical concentration of the at least one substance to be detected in the external environment of the at least partly encapsulated semiconductor substrate, effects on the at least one sensitive region 10/the membrane 18 are (substantially) prevented. The at least one sensor signal thus does not change/scarcely changes despite the (significant) change in the at least one physical variable and/or the at least one chemical concentration of the at least one substance to be detected in the external environment of the at least partly encapsulated semiconductor substrate (on account of the air-, liquid- and/or particle-tight sealing). During production of at least one pressure sensor, the at least one sensing area 12 of the at least one sensitive region 10/the membrane 18 is sealed for example in an air-tight (pressure-tight) fashion from the external environment of the at least partly encapsulated semiconductor substrate.

As an optional development, in the embodiment in FIGS. 1a to 1d, the detection apparatus is formed with an evaluation device 38 and a memory 40 (possibly as a subunit of the evaluation device 38), wherein the evaluation device 38 is configured, during the later operation of the detection apparatus, taking account of at least the at least one sensor signal and an evaluation relation stored in the memory 40, to define and output information regarding the at least one physical variable and/or the at least one substance to be detected. The evaluation device 38 with the memory 40 can be produced for example as an application-specific integrated circuit (ASIC) (formed externally with respect to the semiconductor substrate 14). Likewise, the evaluation device 38 and/or the memory 40 can also be formed on and/or in the semiconductor substrate 14. Moreover, a configurability of the evaluation device 38 and of the memory 40 is not restricted to a specific type of circuit or type of memory.

The evaluation device 38 can be fixed on the printed circuit board 34 by a further adhesive layer 42. A contact pad 46 of the evaluation device 38 can be linked to the contact pad 24 of the semiconductor substrate 14 via a first bonding wire connection 44. A further contact pad 48 of the evaluation device 38 can be connected to the printed circuit board 34 via a second bonding wire connection 50. Optionally, the evaluation device 38 and/or at least one of the bonding wire connections 44 and 50 (together with at least one part of the semiconductor substrate 14) can also be embedded into the at least one encapsulation material 36.

After encapsulating at least the part of the semiconductor substrate 14, at least one first test and/or calibration measurement is carried out, for which purpose the at least one sensor signal of the at least one sensitive region 10 having the at least one sensing area 12 sealed in an air-, liquid- and/or particle-tight fashion from the external environment of the at least partly encapsulated semiconductor substrate 14 is determined as at least one first test and/or calibration signal. The at least one first test and/or calibration signal obtained in this way is well suited to testing/checking whether a further processing of the intermediate product shown in FIG. 1c is still worthwhile. As explained in greater detail below, the at least one first test and/or calibration signal obtained in this way is also advantageously suitable for a later calibration of the detection apparatus produced from at least the semiconductor substrate 14. Moreover, it can be advantageous to temporarily store the at least one first test and/or calibration signal on the memory 40 until the calibration carried out later.

In the embodiment in FIGS. 1a to 1d, the at least one first test and/or calibration measurement is carried out while a (virtually) identical pressure is present at the areas 12 and 22 of the membrane 18 (on account of an absent air access/ pressure access or the air-tight sealing from the external environment). Thus (to a first approximation) the at least one first test and/or calibration signal is measured for "vacuum/ no external pressure". This can also be paraphrased by stating that the at least one first test and/or calibration signal is measured with the membrane 18 being present without pressure during the at least one first test and/or calibration measurement.

Figure 1D:
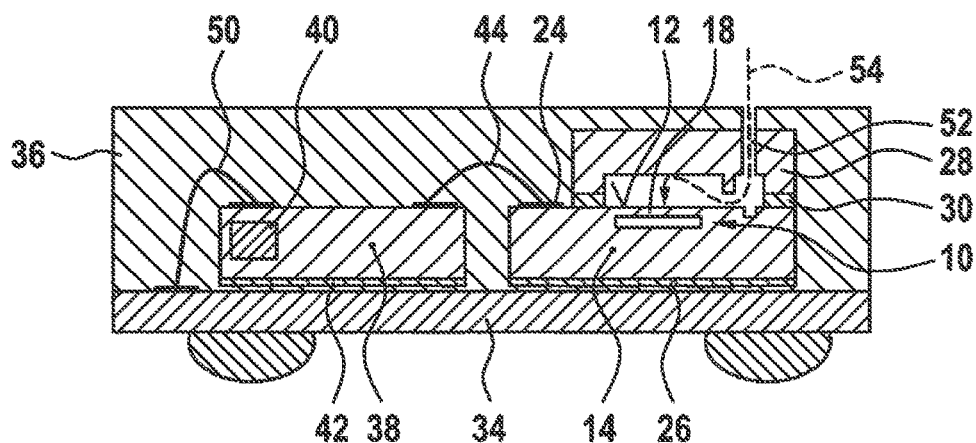

FIG. 1d shows the at least partly encapsulated semiconductor substrate 14 after forming at least one opening 52 at the at least partly encapsulated semiconductor substrate 14 in such a way that at least one air, liquid and/or particle access 54 from the external environment of the at least partly encapsulated semiconductor substrate 14 to the at least one sensing area 12 is created. It is expressly pointed out that the at least one first test and/or calibration measurement is carried out before forming the at least one opening 52. Forming the at least one opening 52 is then carried out such that, on account of the at least one air, liquid and/or particle access 54 being present (in an open fashion), a change in the at least one physical variable and/or the at least one chemical concentration of the at least one substance to be detected in the external environment leads to a change (identifiable on account of the variation of the at least one sensor signal) in the at least one physical variable and/or the at least one chemical concentration at the at least one (exposed) sensing area 12. During production of at least one pressure sensor, for example, by the at least one opening 52, an air access/ pressure access 54 from the external environment of the at least partly encapsulated semiconductor substrate 14 to the at least one sensing area 12 is created, such that an ambient pressure present in the external environment of the at least partly encapsulated semiconductor substrate 14 brings about a deformation of the membrane 18.

After forming the at least one opening 52, in the embodiment of the production method described here, at least one second test and/or calibration measurement is carried out, for which purpose the at least one sensor signal of the at least one sensitive region 10/the membrane 18 is determined with the at least one air, liquid and/or particle access 54 being present (in an open fashion) as at least one second test and/or calibration signal of the at least one second test and/or calibration measurement. By way of example, the at least one second test and/or calibration signal is measured with the membrane 18 being exposed to the atmospheric pressure during the at least one second test and/or calibration measurement.

Afterwards, the evaluation relation (for evaluating the at least one sensor signal by the evaluation device 38 during the later operation of the detection apparatus) is defined at least taking account of the at least one first test and/or calibration signal and the at least one second test and/or calibration signal. By way of example, calibration values/ matching values and/or at least one calibration algorithm/at least one characteristic curve can be defined as the evaluation relation. Despite the easy determinability/-measurability of the at least one first test and/or calibration signal and the at least one second test and/or calibration signal, these signals are advantageously suitable for defining the evaluation relation. By way of example, a linear relation can easily be defined as the evaluation relation taking account of the at least one first test and/or calibration signal and the at least one second test and/or calibration signal. The evaluation relation is subsequently stored on the memory.

Conventionally, most pressure sensors, for compensating for manufacturing fluctuations, are not calibrated until after they have been completed. For that purpose, in accordance with the prior art, the (finished produced) pressure sensors are arranged in a pressure chamber. Afterwards, calibration measurements are carried out with at least two different pressure values in the pressure chamber. Taking account of the calibration measurements carried out in the pressure chamber, the pressure sensors are subsequently intended to be correspondingly matched. However, in the pressure chamber calibration measurements can be carried out (simultaneously) only with a comparatively small number of pressure sensors.

By contrast, the production method described here provides a less complex calibration which nevertheless ensures a high measurement and detection accuracy of the at least one calibrated detection apparatus. In particular, the calibration can be performed without the use of a pressure chamber and can thus be performed more cost-effectively and more simply by comparison with the prior art. Apart from determining the at least one first test and/or calibration signal under "vacuum/no external pressure" during the at least one first test and/or calibration measurement, the at least one second test and/or calibration signal for the at least one second test and/or calibration measurement can be determined at atmospheric pressure/room pressure. (The atmospheric pressure/room pressure can additionally be determined very accurately by a calibrated measuring instrument.) Thus, when performing the production method described here, the conventional measurements in a pressure chamber are no longer necessary for the calibration. Omitting the pressure chamber also allows a simpler contacting of the detection apparatuses. On account of the simpler contacting of the detection apparatuses, a better temperature linking and control is also possible, as a result of which more detection apparatuses can be measured and matched in a shorter time. Even wafer level matching is possible. Moreover, the number of detection apparatuses which can be measured simultaneously is more than would be possible on the basis of a spatial limitation of the conventionally required pressure chamber.

In one advantageous development of the production method described here, a temperature of the membrane 18 (or a temperature in the spatial environment of the membrane 18) can be varied between a plurality of first test and/or calibration measurements and/or between a plurality of second test and/or calibration measurements. The pressure- and temperature-dependent signals of the first test and/or calibration measurements and/or of the second test and/or calibration measurements can subsequently be used for defining a pressure- and temperature-dependent evaluation relation for calibrating the detection apparatus. Consequently, a pressure- and temperature-dependent calibration can also be performed without the use of a pressure chamber. In the conventionally required pressure chamber, a temperature can be varied only slowly, for which reason the pressure chamber has to be occupied for a very long time for each measurement cycle. By contrast, the temperature of the membrane 18 (or the temperature in the spatial environment of the membrane 18) can be varied comparatively rapidly and easily for the first test and/or calibration measurements and/or the second test and/or calibration measurements. In particular, on account of omitting the pressure chamber, in principle it is also possible to employ very rapid temperature ramps. In this case, it is particularly expedient to perform a temperature measurement within the pressure sensor. Moreover, the temperature measurement values of the first test and/or calibration measurements can already be temporarily stored in the memory 40 before forming the at least one opening 52 and/or the temperature measurement values of the second test and/or calibration measurements can also be temporarily stored in the memory 40 after forming the at least one opening 52. In this development, the calibration process/matching process can be performed comparatively with little complexity and less expensively.

In another advantageous development, the at least one item of position information a1 and a2 regarding the (previous or still current) position/location of the semiconductor substrate 14 as part of the wafer 16 is concomitantly taken into account when defining the evaluation relation. By random samples it is possible to find a reliable matching algorithm which at least partly compensates even manufacturing fluctuations/deviations dependent on the position/location of the semiconductor substrate 14 as part of the wafer 16 (e.g. "shading effects" during at least one etching). The matching algorithm can be defined with statistical certainty for all the semiconductor substrates 14 of many wafers 18 by performing once a process of taking a small number of random samples of a wafer 16. Defining the evaluation relation can then be performed while additionally taking account of the at least one item of position information a1 and a2 and the defined matching algorithm.

In an alternative embodiment of the production method described here, the at least one detection apparatus can also be formed with an amplifier device and a memory 40, wherein the amplifier device is configured, during the later operation of the detection apparatus, taking account of at least the at least one sensor signal and an amplification relation stored on the memory 40, to output an amplified signal. In this case, the amplification relation is defined at least taking account of the at least one first test and/or calibration signal, which may also take account of the at least one second test and/or calibration signal and/or taking account of the at least one item of position information a1 and a2 and the defined matching algorithm. The amplification relation is then stored on the memory 40.

Figure 2:
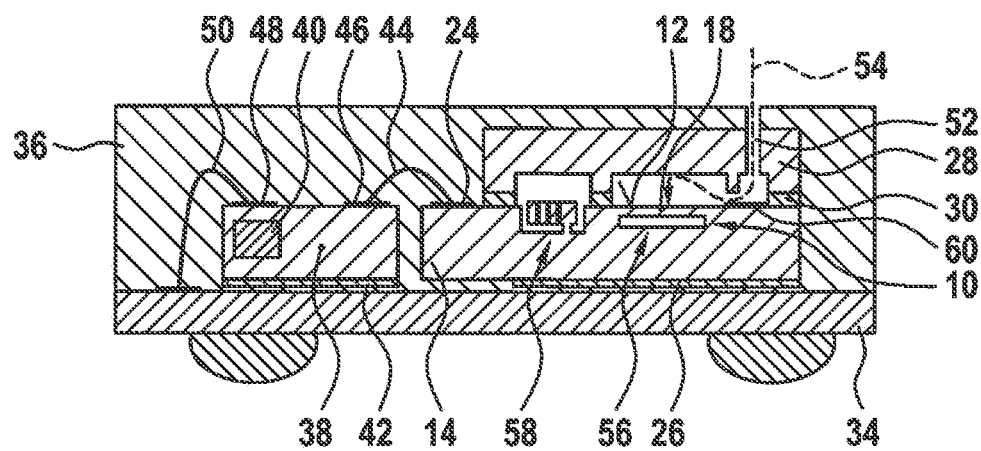
FIG. 2 shows a schematic cross section through a first embodiment of the detection apparatus.

FIG. 2 shows a schematic cross section through a first embodiment of the detection apparatus.

The detection apparatus illustrated schematically in FIG. 2 comprises a semiconductor substrate 14 having at least one sensitive region 10 formed on and/or in the semiconductor substrate 14, wherein the semiconductor substrate 14 is at least partly encapsulated by at least one encapsulation material 36 and/or at least one encapsulation structure 28. At least one sensing area 12 of the at least one sensitive region 10 is exposed by at least one air, liquid and/or particle access 54 which extends in each case from an external environment of the at least partly encapsulated semiconductor substrate 14 at least partly through the at least one encapsulation material 36 and/or the at least one encapsulation structure 28 to the at least one sensing area 12. At least one sensor signal of the at least one sensitive region 10 varies in the case of a change in at least one physical variable and/or at least one chemical concentration of at least one substance to be detected at the sensing area 12 of the respective sensitive region 10. In addition, the detection apparatus has an evaluation device 38 with a memory 40, wherein the evaluation device 38 is configured, taking account of at least the at least one sensor signal and an evaluation relation stored on the memory 40, to define and output information regarding the at least one physical variable and/or the at least one substance to be detected.

The production of the detection apparatus in accordance with the production method explained above can be identified e.g. from the fact that the evaluation relation comprises at least one first test and/or calibration signal which is determined in the case of an air-, liquid- and/or particle-tight sealing of the at least one sensing area 12 of the at least partly encapsulated semiconductor substrate 14 from the external environment as the at least one sensor signal. The production of the detection apparatus with an integrated pressure sensor 56 and an integrated acceleration sensor 58 in accordance with the production method explained above can be demonstrated for example by a highly accurate measurement via pressure (and possibly via temperature). In particular by a statistical analysis of a fault via pressure (and possibly via temperature) it is possible to demonstrate that the calibration was carried out under a vacuum and ambient pressure.

In addition, it is also possible to carry out an analysis of the evaluation device 38/the memory 40 in order to demonstrate the production of the detection apparatus by the production method. On the memory 40, e.g. calibration values/matching values and/or at least one calibration algorithm/at least one characteristic curve are stored as an evaluation relation, from which matching under a vacuum and/or normal ambient pressure can be deduced.

The reference sign 60 refers to an etch stop layer. Instead of the evaluation device 38, the detection apparatus can also have an amplifier device with a memory 40, wherein the amplifier device is configured, taking account of at least the at least one sensor signal and an amplification relation stored on the memory 40, to output an amplified signal, and wherein the amplification relation comprises at least one first test and/or calibration signal which is determined in the case of an air-, liquid- and/or particle-tight sealing of the at least one sensing area 12 of the at least partly encapsulated semiconductor substrate 14 from the external environment as the at least one sensor signal.

Figure 3:
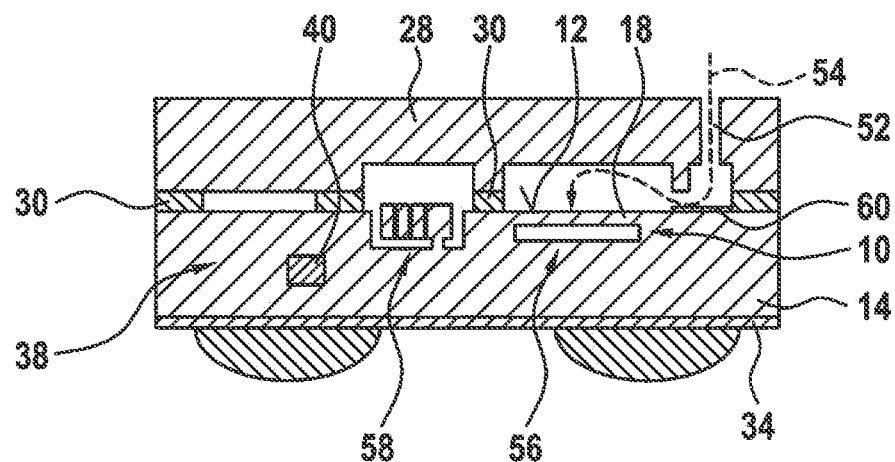
FIG. 3 shows a schematic cross section through a second embodiment of the detection apparatus.

FIG. 3 shows a schematic cross section through a second embodiment of a detection apparatus.

As can be discerned with reference to FIG. 3, the detection apparatus can also be formed as a BARE DIE element. Precisely in the case of a detection apparatus formed as a BARE DIE element, the first test and calibration measurements, or the first and second test and calibration measurements, can be performed at the wafer level. In addition, the use of the at least one encapsulation material 36 can be dispensed with. Accordingly it is also possible, further, to dispense with the at least one encapsulation structure 28 and/or the printed circuit board 34.

What is claimed is:

1. A production method for a detection apparatus, the method comprising:
   forming at least one sensitive region having at least one exposed sensing area on and/or in a semiconductor substrate so that, during later operation of the detection apparatus, at least one sensor signal of the at least one sensitive region varies for a change in at least one physical variable and/or at least one chemical concentration of at least one substance to be detected at the sensing area of the respective sensitive region;
   encapsulating at least one part of the semiconductor substrate so that the at least one sensing area of the at least one sensitive region is sealed in an air-, liquid- and/or particle-tight fashion from an external environment of the at least partly encapsulated semiconductor substrate; and
   forming at least one opening at the at least partly encapsulated semiconductor substrate so that at least one air, liquid and/or particle access from the external environment of the at least partly encapsulated semiconductor substrate to the at least one sensing area is created;
   wherein before forming the at least one opening, at least one first test and/or calibration measurement is performed, for which the at least one sensor signal of the at least one sensitive region having the at least one sensing area sealed in an air-, liquid- and/or particle-tight manner from the external environment of the at least partly encapsulated semiconductor substrate is determined as at least one first test and/or calibration signal of the at least one first test and/or calibration measurement.

2. The production method of claim 1, wherein, after forming the at least one opening, at least one second test and/or calibration measurement is performed, for which the at least one sensor signal of the at least one sensitive region, given the presence of the at least one of an air access, a liquid access and a particle access is determined as at least one second test and/or calibration signal of the at least one second test and/or calibration measurement.

3. The production method of claim 1, wherein the detection apparatus includes an evaluation device and a memory, wherein the evaluation device is configured, during the later operation of the detection apparatus, taking account at least of the at least one sensor signal and an evaluation relation stored on the memory, to define and output information regarding the at least one physical variable and/or the at least one substance to be detected, and wherein the evaluation relation is defined at least taking account of the at least one first test and/or calibration signal and is stored on the memory.

4. The production method of claim 1, wherein the detection apparatus includes an amplifier device and a memory, wherein the amplifier device is configured, during the later operation of the detection apparatus, taking account of at least the at least one sensor signal and an amplification relation stored on the memory, to output an amplified signal, and wherein the amplification relation is defined at least taking account of the at least one first test and/or calibration signal and is stored on the memory.

5. The production method of claim 3, wherein the evaluation relation is defined at least taking account of the at least one first test and/or calibration signal and the at least one second test and/or calibration signal.

6. The production method of claim 3, wherein the at least one sensitive region is formed on and/or in the semiconductor substrate, which is part of a wafer, wherein the semiconductor substrate is structured from the wafer, and wherein at least one item of position information regarding a position of the semiconductor substrate as part of the wafer is concomitantly taken into account by defining the evaluation relation or the amplification relation.

7. The production method of claim 1, wherein the detection apparatus includes at least one of a pressure sensor, a blood pressure sensor, a sound sensor, a microphone, a temperature sensor, a chemical sensor, a gas sensor, an odour sensor, a liquid sensor and a particle sensor.

8. The production method of claim 1, wherein a capacitor having a membrane that at least partly spans a cavity formed in the semiconductor substrate is formed as the at least one sensitive region so that a change in a pressure present at the sensing area of the membrane as the at least one physical variable brings about a deformation of the membrane, as a result of which a capacitance of the capacitor varies and a current intensity and/or voltage signal, dependent on the capacitance of the capacitor, as the at least one sensor signal varies.

9. The production method of claim 8, wherein the at least one first test and/or calibration signal is measured with the membrane being present without pressure during the at least one first test and/or calibration measurement and the at least one second test and/or calibration signal is measured with the membrane being exposed to the atmospheric pressure during the at least one second test and/or calibration measurement.

10. The production method of claim 9, wherein a temperature of the membrane is varied between a plurality of first test and/or calibration measurements and/or between a plurality of second test and/or calibration measurements.

11. A detection apparatus, comprising:
    a semiconductor substrate having at least one sensitive region formed on and/or in the semiconductor substrate, wherein the semiconductor substrate is at least partly encapsulated by at least one encapsulation material, and/or at least one encapsulation structure, wherein at least one sensing area of the at least one sensitive region is exposed by at least one of an air access, a liquid access and a particle access which extends in each case from an external environment of the at least partly encapsulated semiconductor substrate at least partly through the at least one encapsulation material and/or the at least one encapsulation structure to the at least one sensing area, and wherein at least one sensor signal of the at least one sensitive region varies for a change in at least one physical variable and/or at least one chemical concentration of at least one substance to be detected at the sensing area of the respective sensitive region; and
    an evaluation device having a memory, wherein the evaluation device is configured, taking account of at least the at least one sensor signal and an evaluation relation stored on the memory, to define and output information regarding the at least one physical variable and/or the at least one substance to be detected;
    wherein the evaluation relation includes at least one first test and/or calibration signal which is determined in the case of an air-, liquid- and/or particle-tight sealing of the at least one sensing area of the at least partly encapsulated semiconductor substrate from the external environment as the at least one sensor signal.

12. A detection apparatus, comprising:
a semiconductor substrate having at least one sensitive region formed on and/or in the semiconductor substrate, wherein the semiconductor substrate is at least partly encapsulated by at least one encapsulation material and/or at least one encapsulation structure, wherein at least one sensing area of the at least one sensitive region is exposed by at least one of an air access, a liquid access and a particle access which extends in each case from an external environment of the at least partly encapsulated semiconductor substrate at least partly through the at least one encapsulation material and/or the at least one encapsulation structure to the at least one sensing area, and wherein at least one sensor signal of the at least one sensitive region varies for a change in at least one physical variable and/or at least one chemical concentration of at least one substance to be detected at the sensing area of the respective sensitive region; and
an amplifier device having a memory, wherein the amplifier device is configured, taking account of at least the at least one sensor signal and an amplification relation stored on the memory, to output an amplified signal;
wherein the amplification relation includes at least one first test and/or calibration signal which is determined in the case of an air-, liquid- and/or particle-tight sealing of the at least one sensing area of the at least partly encapsulated semiconductor substrate from the external environment as the at least one sensor signal.

* * * * *